United States Patent [19]
Loddeke et al.

[11] Patent Number: 5,964,590
[45] Date of Patent: Oct. 12, 1999

[54] PERMANENTLY LUBRICATED DENTAL PROPHYLAXIS ANGLE

[75] Inventors: Gerald Ray Loddeke, O'Fallon; James R. Thurman, III, Cadet; Mark M. Rose, Crystal City, all of Mo.

[73] Assignee: Young Dental Manufacturing Company, Earth City, Mo.

[21] Appl. No.: 09/039,300

[22] Filed: Mar. 14, 1998

[51] Int. Cl.⁶ ........................................ A61C 3/06
[52] U.S. Cl. ............................ 433/125; 433/126
[58] Field of Search .................... 433/125, 126, 433/166, 114, 116, 133, 134, 115

[56] References Cited

U.S. PATENT DOCUMENTS

| | | |
|---|---|---|
| 2,098,317 | 11/1937 | Staunt . |
| 3,163,934 | 1/1965 | Wiseman ................................. 433/125 |
| 3,707,042 | 12/1972 | Talaga . |
| 4,486,175 | 12/1984 | Fisher et al. . |
| 4,947,942 | 8/1990 | Lightle et al. . |
| 5,348,473 | 9/1994 | Kivlighan, Jr. ......................... 433/114 |
| 5,352,119 | 10/1994 | Sakurai . |
| 5,484,284 | 1/1996 | Bailey ..................................... 433/125 |
| 5,642,995 | 7/1997 | Bailey . |
| 5,645,426 | 7/1997 | Grim et al. . |
| 5,683,247 | 11/1997 | Bailey . |
| 5,749,728 | 5/1998 | Bailey ..................................... 433/125 |

Primary Examiner—Gene Mancene
Assistant Examiner—Philogene Pedro
Attorney, Agent, or Firm—Polster, Lieder, Woodruff & Lucchesi

[57] ABSTRACT

A maintenance-free dental prophylaxis angle includes a one-piece body including a sleeve and a head. The sleeve and head define intersecting bores. A one-piece drive gear including an enlarged bearing part and a forward gear end is journaled directly in the sleeve and held axially between a retaining ring engaging the rear of the enlarged bearing part and a ball engaging the forward gear end. A one-piece driven gear is journaled solely in a cap which is press fit in the head bore The driven gear is engaged and driven by the drive gear. The driven gear includes an upper bur tube and a lower gear part. The gear part of the driven gear rests on the ball, and is restrained from axial movement by the cap and the ball, which forms a thrust bearing for the driven gear. A dental tool is connected to the bur tube of the driven gear, and forms a seal with the cap.

25 Claims, 5 Drawing Sheets

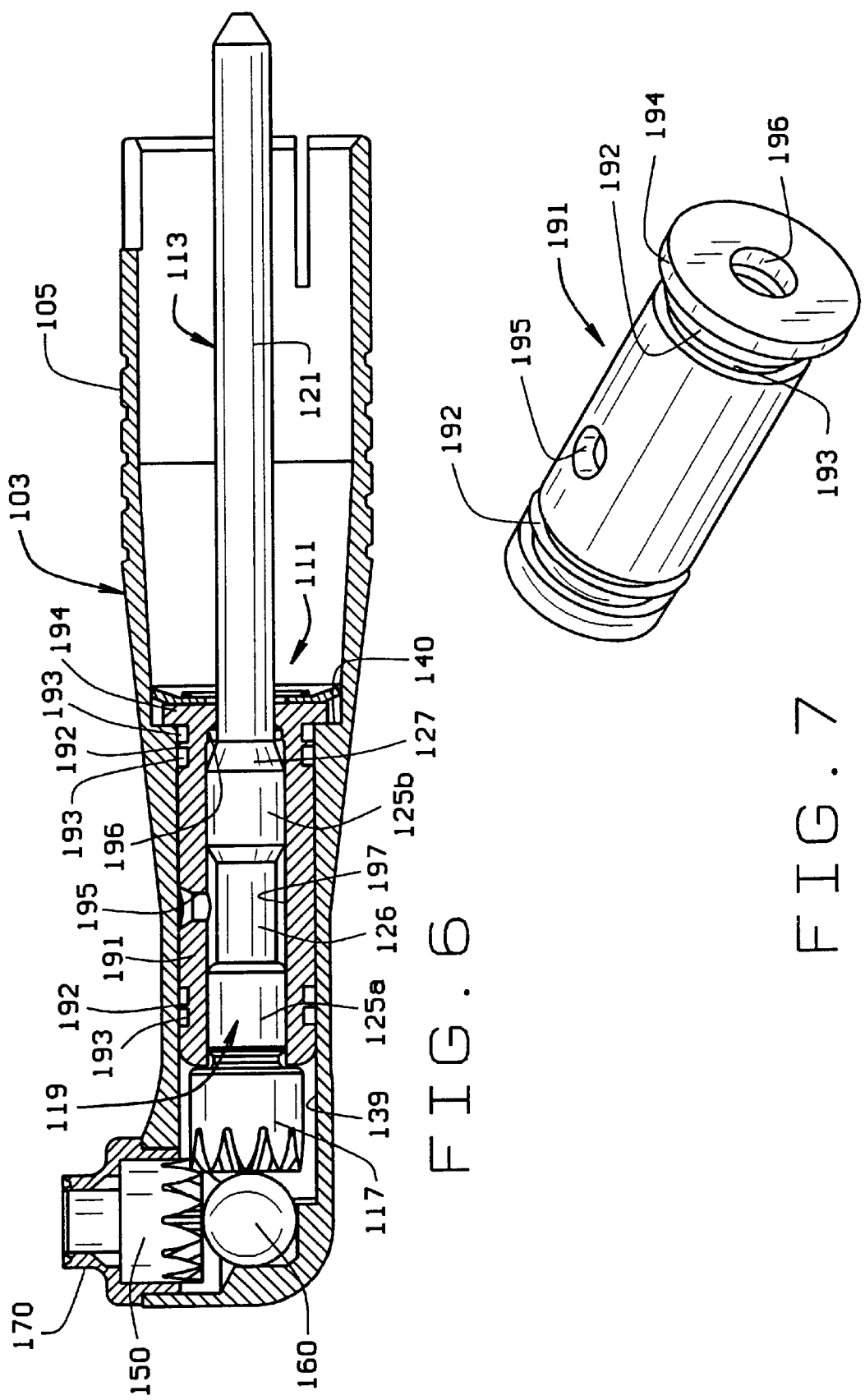

PERMANENTLY LUBRICATED DENTAL PROPHYLAXIS ANGLE

BACKGROUND OF THE INVENTION

This invention relates to dental prophylaxis angles (commonly referred to as prophy angles). It has particular application to a low-cost prophy angle which need not be lubricated even after repeated autoclave cycles.

Most prophy angles currently available are either low-cost disposable prophy angles which are discarded after each use or else expensive reusable metal prophy angles which require a considerable amount of care to maintain. A reusable angle must not only be autoclaved between uses or procedures to ensure that the angle is sterile for the next procedure, but it must be maintained. Reusable angles need to be lubricated to run smoothly. The lubrication, however, breaks down and is lost over time through use and because of the autoclaving. Some manufacturers recommend that prophy angles be lubricated after every ten hours of use. If the angle is not lubricated, the angle will eventually seize up and become inoperable. Through use, debris may also find its way into the angle's head. This debris can interfere with the operation of the angle's gears, and can ultimately ruin the gears. Reusable angles must therefore be periodically disassembled for both cleaning and lubricating. Many dentists and hygienists do not lubricate and clean their prophy angles on a regular schedule. If the angles are not lubricated and cleaned periodically, they will eventually fail.

An example of an expensive, high-quality reusable prophy angle is the TS2™ angle sold by Young Dental Manufacturing Company of Earth City, Mo., the assignee of the present invention. This angle is shown as prior art in FIG. 1 and described in Bailey, U.S. Pat. No. 5,683,247, assigned to Young Dental Manufacturing Company. The disclosure of Bailey, U.S. Pat. No. 5,683,247 is incorporated herein by reference.

An early attempt to produce a lower-cost prophy angle was made by Young Dental Manufacturing Company around 1975, with a "Model C" reusable prophy angle. This angle used a two-piece body and head which were threaded together. A cap was press fit into the head. The driven gear of the angle included a bur tube but no lower stem. It was rotatably mounted entirely in the cap and sat on a flat shelf machined into the head. This design proved to be unacceptable commercially and was withdrawn from the market.

Bailey, U.S. Pat. No. 5,683,247 describes a relatively low-cost prophy angle which can be used for an extended period, on the order of a year or more, without maintenance. A commercial device made in accordance with that patent has been on sale under the mark CARE-FREE® by Young Dental Manufacturing Company for over two years and has been commercially successful. The cost of manufacturing the angle, however, has been higher than desired.

Another alternative to single-use disposable prophy angles and expensive reusable angles has been proposed in Wiseman, U.S. Pat. No. 3,163,934. That patent discloses a relatively low-cost prophy angle whose body, cap, and drive shaft bearing are made of polypropylene, and whose drive gear, driven gear, bearing-locking collar, and ball thrust bearing are made of metal. A small quantity of silicone lubricant is packed into the head (nose) of the angle. Although this angle is designed to be sealed and to be repeatedly sterilized, it is not sufficiently sealed to prevent intrusion of materials from the patient's mouth or leakage of lubricant during use, and it does not lend itself to repeated autoclaving. Moreover, its construction does not lend itself to precise alignment of the moving parts, thereby increasing the difficulty of making the instrument run smoothly, quietly, and reliably.

SUMMARY OF THE INVENTION

One object of the present invention is to provide a dental prophy angle which need not be lubricated or cleaned of debris during a long useful life.

Another object is to provide such an angle which includes an effective means for sealing the angle during use.

Another object is to provide such an angle which may be produced so inexpensively that it may be economically replaced after a period of time, such as three months, six months or one year.

Another object is to provide such an angle which includes a body that is simple to machine from bar stock.

Other objects will become apparent to those skilled in the art in light of the following disclosure and accompanying drawings.

In accordance with one aspect of the invention, generally stated, a dental prophylaxis angle is provided which includes a one-piece body having a sleeve, a neck, and a head. The sleeve and neck define a continuous bore which intersects a bore in the head. A drive gear is rotatably mounted in the sleeve and neck. The drive gear includes a gear part and a shaft part machined from a single piece. The gear part is larger than the shaft part. The shaft extends slightly beyond the rear end of the prophy angle to be grasped by the collet of a dental handpiece, such as the Doriot nose of an air motor handpiece. A driven gear is received in the head bore to be driven by the drive gear. The driven gear includes an upper shaft or bur tube and a gear part. Unless otherwise indicated, the term "bur tube" is used in the specification and claims to include any such shaft, whether hollow or not. A thrust bearing, preferably in the form of a hard ball, is inserted in the one-piece body in the area of the intersection of the bores. Both the drive gear and the driven gear are restrained from axial movement by the ball. Preferably, all of the parts of the prophy angle are formed of metal. Most preferably, the body and cap are made by machining, and the cap is press fit into the head of the body.

Because the head of the preferred embodiment is made smaller in height than the head of previously known angles, the size of the stock from which the angle is machined may be smaller, and the tools used for machining the body may be simplified. This approach allows the height of the cap to determine the height of the assembled head of the prophy angle.

In accordance with another aspect of the invention, a thrust bearing is provided for the drive gear of the angle, the thrust bearing comprising a sheet-metal retaining ring having a plurality of generally radially extending arms which engage an inner wall of the sleeve portion of the one-piece body. In one embodiment, the gear part of the drive gear of the prophy angle is directly journaled in a reduced diameter portion of the bore in the neck, and a rearwardly facing shoulder, at the rear of the gear part, is held by the sheet-metal retaining ring. Preferably, a washer is interposed between the retaining ring and the shoulder on the drive gear. A rearwardly facing shoulder at the rear of the neck bore forms a convenient stop for the retaining ring. The sheet metal retaining ring and washer are far less expensive than the separate bushing of Bailey, U.S. Pat. No. 5,683,247. Moreover, boring the reduced diameter portion of the sleeve portion requires only a single step and reduces the chances for error in forming a perfectly aligned and sized bearing for the drive shaft. The drive shaft of the drive gear may include a bearing portion which is larger in diameter than the gear part, approximately the diameter of the inserted bushing of Bailey, U.S. Pat. No. 5,683,247. The bearing portion may thus include a relieved central part that provides a large volume for grease for extended lubrication of the drive gear.

In another embodiment, the body is formed of a low-cost material such as aluminum, and a separate bushing is inserted and held by a sheet-metal retaining ring having a plurality of generally radially extending arms which engage an inner wall of the sleeve. The separate bushing includes a lubricant opening to allow the drive gear and bushing assembly to be lubricated before the assembly is installed in the one-piece body. The separate bushing is preferably additionally or alternatively held by integral annular barbs machined in the outside surface of the bushing. The separate bushing may be formed of a good bearing material, such as brass, to increase the life of the angle. The use of inexpensive material to form the one-piece body offsets much or all of the additional cost of the separate bushing.

In accordance with another aspect of the invention, a metal cap is mounted, preferably press fit, in the head bore to close the head bore and retain the driven gear in place in the head. The driven gear is journaled in the cap, the cap forming the sole radial (rotational) bearing for the driven gear. Preferably, the interior of the cap is sized to form a rotational bearing for the enlarged gear part of the driven gear and, most preferably, for the bur tube. Because the driven gear is rotationally mounted entirely in the cap, making substantially point contact with the thrust bearing ball, it is substantially unaffected by slight misalignments of the cap with respect to the body. In the embodiment utilizing low-cost material for the one-piece body, this arrangement also eliminates the need for a separate bushing for the driven gear.

A dental tool such as a prophylaxis cup is connected to the bur tube of the driven gear, and an elastomeric portion of the tool forms a seal with the cap. Preferably, the cap includes a hollow stem surrounding the bur tube, and a knife edge on the hollow stem cuts into an elastomeric ring on the dental tool, in accordance with Bailey, U.S. Pat. Nos. 5,484,284, the disclosure of which is hereby incorporated by reference. The cap is preferably provided with a protective wall around its hollow stem, as described in Bailey, U.S. Pat. 5,642,995, the disclosure of which is hereby also incorporated by reference. The cap forms a tight fit with the body. The seal between the dental tool and the cap substantially prevents foreign material from entering the body and reduces or eliminates the need to clean the interior of the prophy angle. It also prevents grease from leaving the angle.

The volume in the head around the ball acts as a lubricant reservoir. Lubricant reservoirs are also formed by a volume in the cap between a relief area in the cap and the bur tube and also by a volume in the neck of the body surrounding a relieved space in the bearing portion of the drive gear. A food-grade lubricant which can withstand many autoclaving cycles is preferably used. The angle thus does not have to be lubricated during its useful life.

Preferably, the angle cannot easily be disassembled, and can be used for an extended period of time, for example three months, six months, or one year, without requiring any maintenance. Because the construction permits the angle to be produced at low cost, at the end of its useful life the angle can be replaced with a new angle.

Other aspects of the invention will become apparent to those skilled in the art in light of the following description of the preferred embodiment.

BRIEF DESCRIPTION OF THE DRAWINGS

FIG. 6 is a cross-sectional view of another embodiment of dental prophy angle of the present invention; and FIG. 7 is a view in perspective of a bushing for use in the angle of FIG. 6.

DESCRIPTION OF THE PREFERRED EMBODIMENTS

Figure 1:
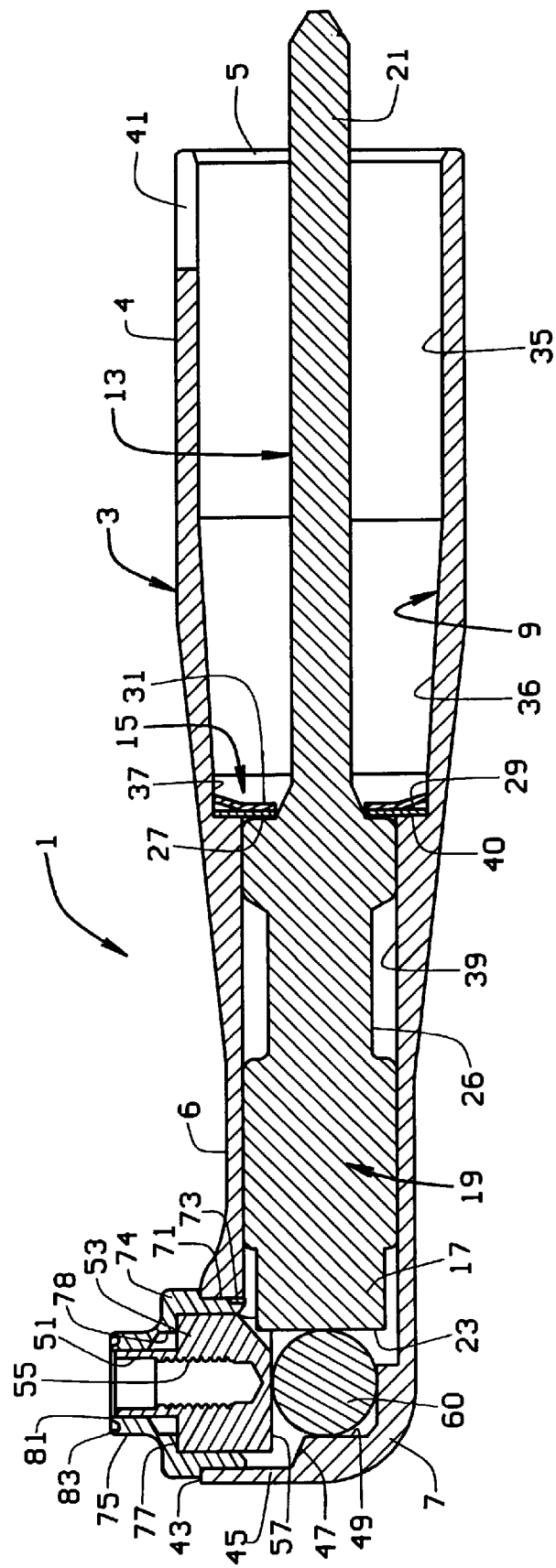
FIG. 1 is a cross-sectional view of a dental prophy angle of the present invention.
Figure 2:
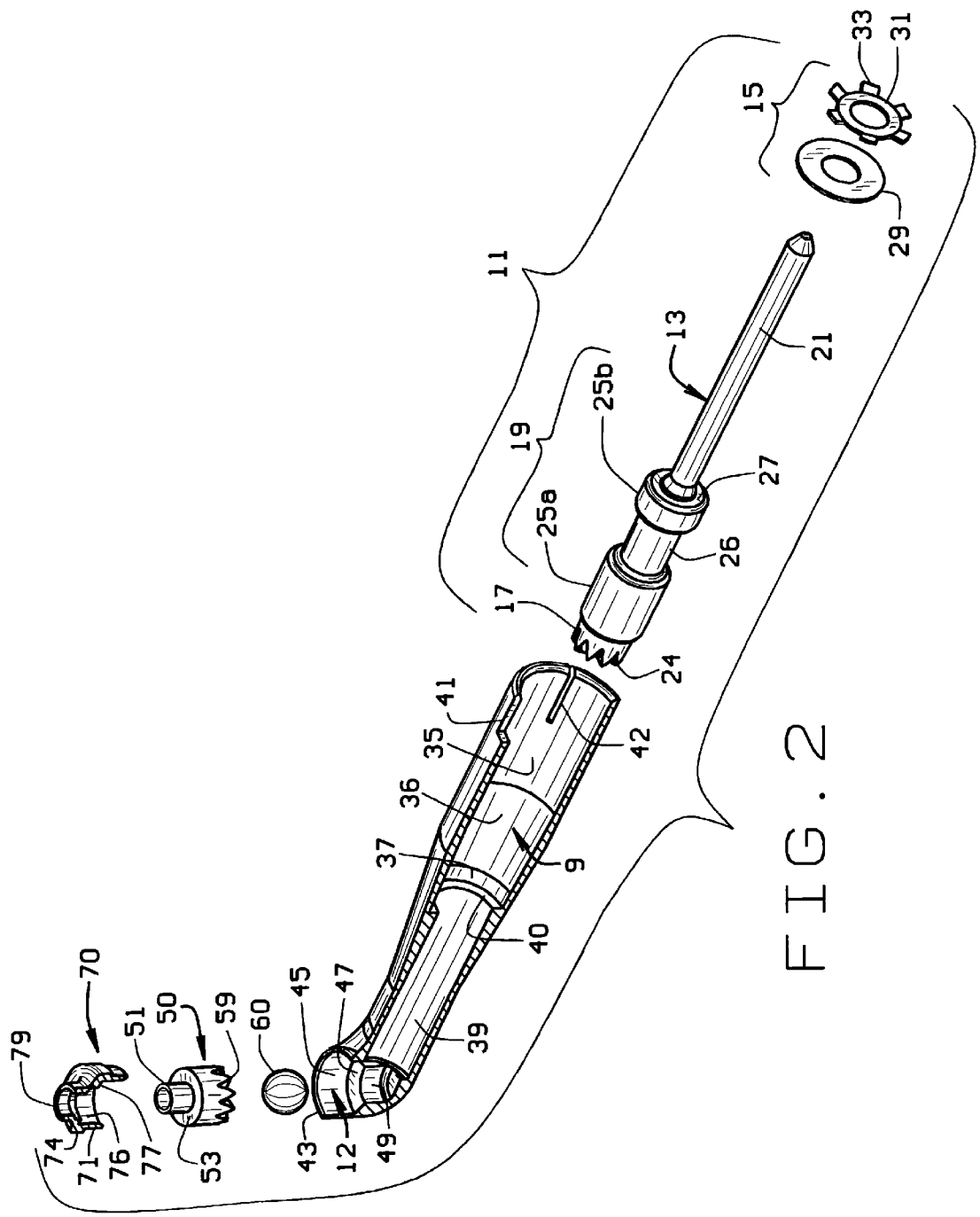
FIG. 2 is an exploded view, partially cut away, in perspective of the prophy angle of FIG. 1.
Figure 3:
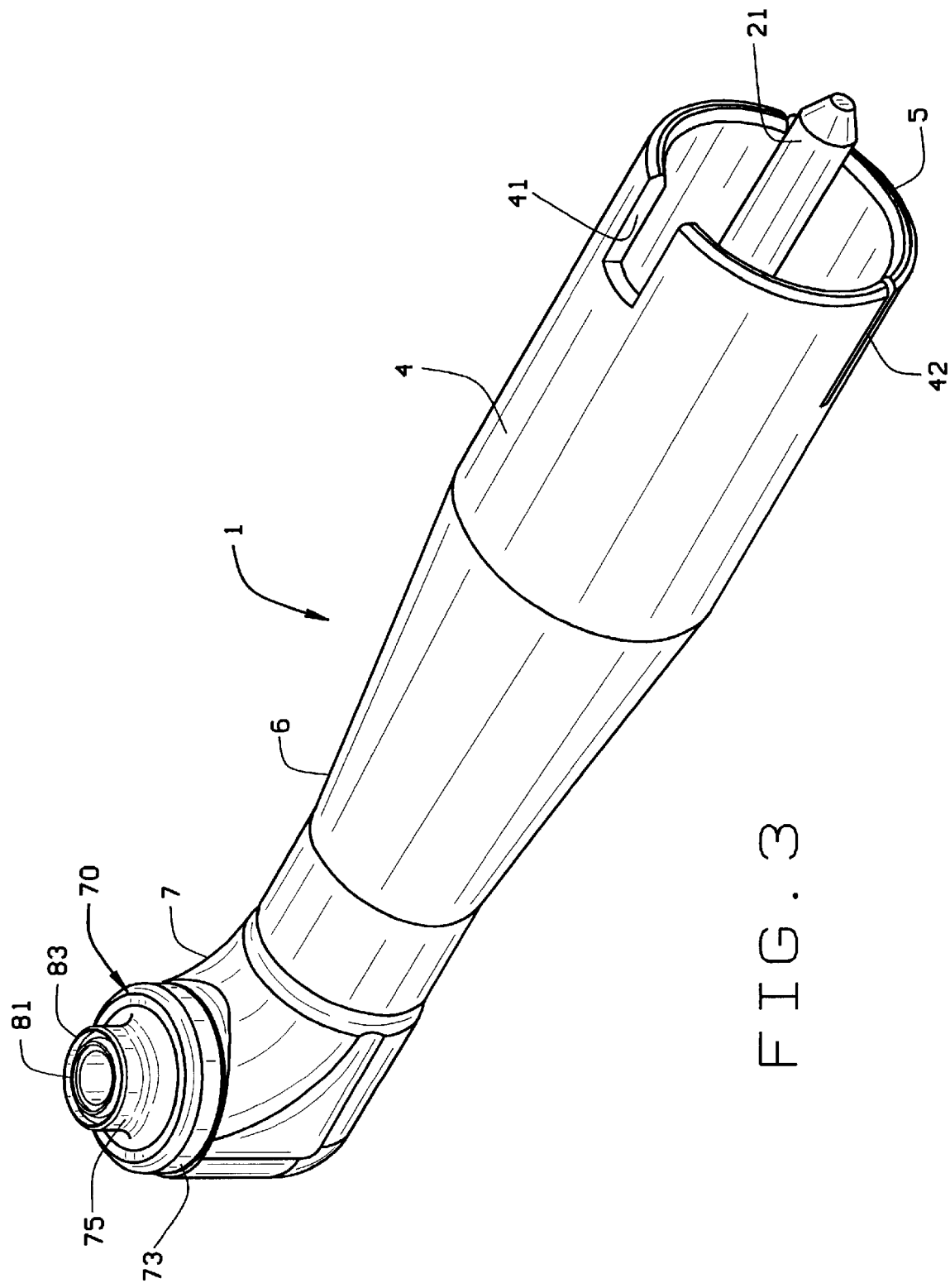
FIG. 3 is a view in perspective of the assembled prophy angle of FIGS. 1 and 2.
Figure 4:
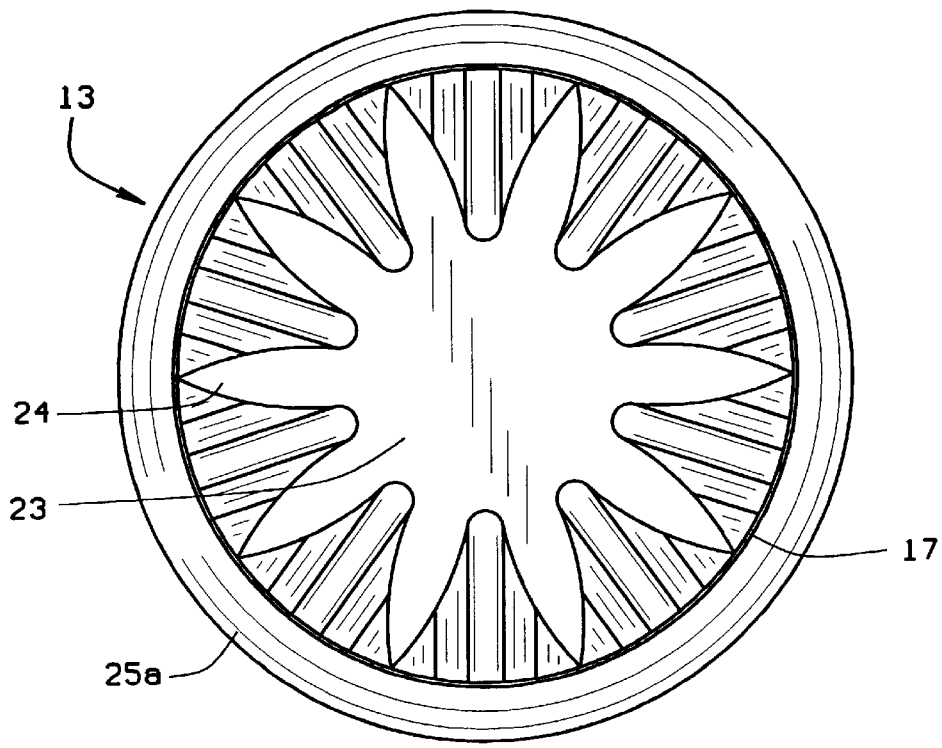
FIG. 4 is a view in front end elevation of a drive gear of the angle.

Referring now to the drawings, and in particular to FIGS. 1–5, reference numeral 1 indicates a preferred embodiment of a dental prophy angle of the present invention. Angle 1 includes a one-piece metal body 3 having a sleeve 4 with an open back end 5, a neck 6, and a head 7.

Sleeve 4 and neck 6 define an axially extending body bore 9 which receives a drive assembly 11. Head 7 defines an upwardly opening bore 12, as described more fully hereinafter. The bores 9 and 12 intersect at 90° in the head 7.

Drive assembly 11 includes a drive gear 13 and a thrust bearing assembly 15.

Drive gear 13 includes a drive gear part 17, a bearing part 19, and a rearwardly extending shaft 21. As shown particularly in FIG. 4, the flat forward face 23 of the gear part 17 has ten gear teeth 24 cut in it. The gear teeth 24 are modified bevel gear teeth, formed in the same manner as are the teeth of the commercially available CARE-FREE® angle.

Bearing part 19 is larger than the gear part 17 and extends back from the gear part 17 through the bore 39 in neck 6 of the one-piece body. The bearing part 19 includes two spaced apart bearing sections 25a and 25b of increased diameter which define bearing surfaces for the drive assembly and a central portion 26 which is smaller in diameter. The rearward bearing section 25b ends in a radially extending rearwardly facing shoulder 27. The bearing sections 25a and 25b have substantially the same diameter as the bushing of Bailey, U.S. Pat. No. 5,683,247; they are thus larger than the gear part 17 of the drive gear 13.

Shaft 21 extends beyond the open end 5 of the body 3 and is sized to be received by the collet of a handpiece, such as a Doriot type handpiece.

Thrust bearing assembly 15 includes a bronze washer 29 and a retaining ring 31. The washer 29 is nominally 0.028" thick, with an outside diameter of 0.314" and an inside diameter of 0.133". The retaining ring 31 is illustratively a Waldes Truarc®5005-31 circular push-on internal series ring sized to fit a three-sixteenths inch bore, and having an inside diameter of 0.136". The retaining ring 31 includes six prongs 33 which are flexed rearwardly when the ring is installed in the bore 9. The ring 31 is formed of stainless steel (PH 15-7 Mo or equivalent; AISI 632-AMS 5520) and has a thickness of approximately 0.012". It is designed for a thrust load of eighty pounds when installed in soft cold rolled steel bores.

Bore 9 includes, from its open rear 5, a cylindrical section 35 sized to fit the Doriot nose of a dental handpiece, a tapered section 36, a smaller cylindrical section 37 sized to receive the thrust bearing assembly 15, and a yet smaller cylindrical section 39 in neck 6 sized to journal drive gear bearings 25*a* and 25*b*. The rearward face 40 of the cylindrical bearing section 39 forms a shoulder against which the washer 29 of the thrust bearing assembly 15 is held by the retaining ring 31. The forward cylindrical section 39 extends into the head 7 of the body 3, stopping slightly short of the axis of the head bore 12.

At the rear of the body sleeve 4 are cut a standard positioning slot 41 and a pair of expansion slits 42. The positioning slot 41 may be 0.187" long and 0.100" wide. The expansion slits 42 may be 0.250" long and 0.016" wide. The expansion slits 42 permit the end of the sleeve 4 to expand slightly when the angle is placed on a handpiece, and thus create a size-on-size frictional fit with the nose of the handpiece. The slot 41 embraces a pin or protrusion on the Doriot nose and holds the angle body angularly with respect to the handpiece, as is standard in the art.

The flat upper face 43 of the head 7 is below the apex of the sleeve 4 as shown in FIG. 1. In the illustrative embodiment, the sleeve 4 has a radius of about 0.21", and the upper corner of the head as viewed in front elevation extends about 0.225" from the axis of the bore 9, thereby setting the minimum radius of the stock from which the body 3 may be machined. It will be seen that the maximum radial extent of the head, measured from the axis of the body bore 9, is less than 10% greater than the radius of the sleeve 4.

Head bore 12 includes an enlarged upper portion 45, an intermediate beveled portion 47 and a smaller-diameter lower portion 49. The axes of the head bore 12 and the body bore 9 intersect at an angle of 90° in the lower portion 49.

Figure 5:
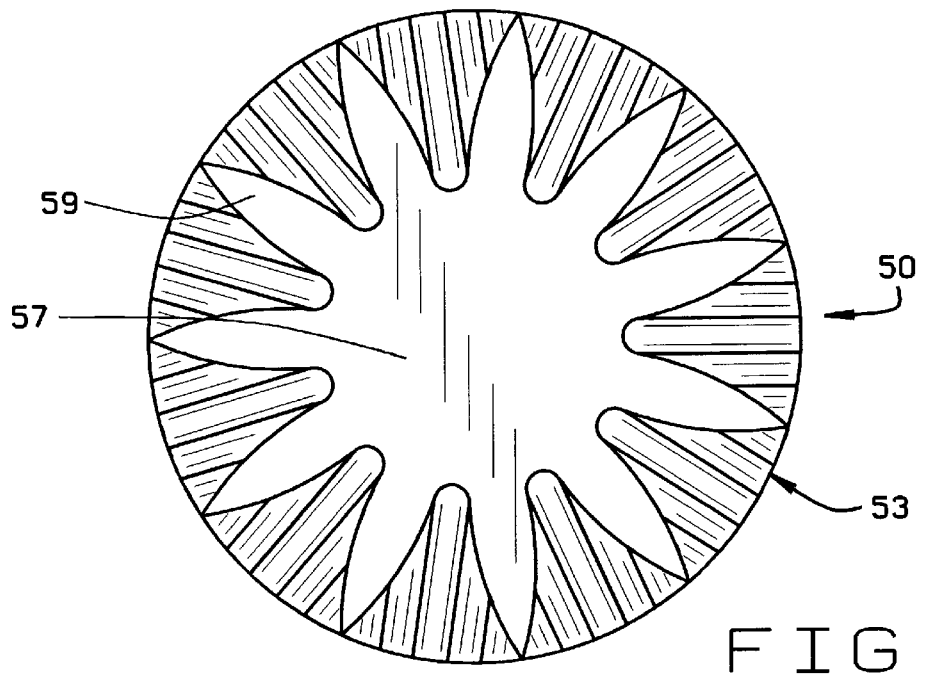
FIG. 5 is a bottom plan view of a driven gear of the angle.

Head bore 12 receives a driven gear 50. The driven gear 50 includes an upper shaft or bur tube 51 and a gear part 53, machined from one piece of metal. The bur tube 51 is bored and threaded as at 55 to receive the shaft of a dental tool such as a prophylaxis cup. As shown in FIG. 5, the flat lower face 57 of the gear part 53 has eleven gear teeth 59 cut in it. The gear teeth 59 are modified bevel gear teeth, formed in the same manner as are the teeth of the commercially available CARE-FREE® angle to provide smooth engagement and rotation with the similar gear teeth 20 of the drive gear part 17.

A ball 60 is press fitted in the lower portion 49 of the head bore 12. The ball is preferably a 0.1563" diameter ball (sphericity of 0.000025") made of Grade 25 chrome steel (SAE 52100 or equivalent) with a Rockwell hardness of C60–67 and a specific gravity of 7.833. The geometric center of the ball 60 is at the intersection of the axis of body bore 9 and the axis of head bore 12. The ball 60 acts as a thrust bearing for both the drive gear 20 and the driven gear 50.

A cap 70 is received in upper part 45 of head bore 12. The cap 70 provides the sole radial (rotational) support for the driven gear 50 and secures gear 50 in the head bore to prevent excess axial movement of gear 50 relative to head 7. Cap 70 includes, from its bottom, a trunk 71 including a slightly smaller diameter lead section 73 at its lower end, an annular flange 74, and a stem 75. The trunk 71 is press fit into the upper part 45 of head bore 12. The lead section 73 pilots the cap into the bore 12. By way of example, the trunk 71 may have a nominal diameter of 0.251", the lead section 73 a nominal diameter of 0.249", and the upper head bore 45 a nominal diameter of 0.250". Annular flange 74 extends radially outwardly from trunk 71 over the top surface 43 of head 7.

Within the cap 70 are a cap bore 76, a shoulder 77, an intermediate bore 78, and a stem bore 79. The cap bore 76 is sized to journal the gear part 53 of driven gear 50, and the stem bore 78 is sized to journal the bur tube part S1 of the driven gear 50. The upper face of the gear part 53 is adjacent the shoulder 77. The relative axial positions of the shoulder 77 and the lower face of the flange 74 are carefully fixed to determine how far axially upward the driven gear 50 is permitted to move.

The flat ends 23 and 57 of the drive gear and driven gear, respectively, engage the ball 60. The ball 60 thus acts as an axial bearing for both gears. Under load, the driven gear 50 is pushed against the ball 60 which thus acts as a thrust bearing for the driven gear 50. The depth of the lower head bore portion 49 is carefully controlled to determine the position of the ball 60, hence the extent of downward movement which the driven gear 50 is allowed. A total end play of a few thousandths of an inch is preferred for both the driven gear and the drive gear.

The upper edge of the stem 75 on the cap 70 includes a knife edge 81 surrounding the open upper end of the stem bore 79, and a protective wall 83 surrounding the knife edge 81, all as described in detail in Bailey, U.S. Pat. No. 5,642,995. Bur tube 51 of driven gear 50 extends up through bore 79 to near the top of stem 75.

The body 3 is preferably machined from a CA360 brass rod and then chrome plated. The drive gear 13 and cap 70 are machined from 303 stainless steel rods. The driven gear 50 is machined from a phos-bronze rod.

Angle 1 is assembled by pressing the ball 60 into the bottom of the lower part 49 of head bore 12. Lubricant is applied to the inside of the cap 70, leaving a thick coating in the area of intermediate bore 78, and the driven gear 50 is pushed into the cap 70. This assembly is then pressed into the upper part 45 of the head bore 12 until the cap flange 74 seats on the upper face 43 of the head. Excess lubricant is applied around the ball 60 to fill the volume around the ball. Lubricant is applied around the bearing part 19 of the drive gear 13, leaving a heavy layer in the central portion 26, and the drive gear 13 is pushed gear-first into engagement with the ball 60. The washer 29 is dropped into place against the shoulder 40, and the retaining ring 31 is forced against it to lock the drive gear in place. If desired, a dental tool, such as a prophy cup, is threaded into the threads 55 of driven gear bur tube 51. It has been found that if the angle 1 is operated without a cup or other tool which seals with the knife edge 81 lubricant could be forced out of the top of the stem 75. The angle thus does not have to be lubricated during its useful life so long as it is used with cups and other tools which seal with the knife edge 81.

The seal between the cap and the cup prevents foreign material, which could damage and otherwise contaminate the gears, from entering the body. The angle 1 can therefore be used for a considerable period of time without requiring any maintenance from the dentist or hygienist. The fact that the body is machined as a single piece reduces the number of joints in the angle and thus reduces the possibility of foreign matter entering the angle.

Because the angle body is machined as a single piece, manufacture and assembly of the angle 1 is less expensive than assembly of multi-piece bodies. Further, because the cap 70 and retaining ring 31 are force fit into the body, rather than being threaded into the body, as is currently done, mating threads on the cap and bushing, and in the body do not have to be formed. This further reduces the cost of manufacturing the angle. Because the angle does not have to be maintained and because it is less expensive to manufacture than current metal angles, after a period of time, for example one year, the angle 1 can be replaced with a new angle.

A second embodiment of dental angle of the present invention is shown in FIGS. 6 and 7.

This embodiment is in most respects identical with the first embodiment. The retaining ring 131, driven gear 150, ball 160, and cap 170 may be identical with the corresponding parts 31, 50, 60, and 70 of the first embodiment. The washer 29 is eliminated.

The body 103 differs from the body 3 of the first embodiment in two principal respects. First, it is machined from 6061-T6 aluminum stock and anodized. Second, it is provided with a series of annular grooves 105 around the sleeve 104 to give the user a solid grip.

The drive assembly 111 includes, in addition to the retainer 131, a drive gear 113 and a bushing 191.

Drive gear 113 includes a drive gear part 117 and a rearwardly extending shaft 121 which are identical with the corresponding parts of the drive gear 13 of the first embodiment. Bearing part 119 includes two spaced apart bearing sections 125a and 125b of increased diameter which define bearing surfaces for the drive assembly and a central portion 126 which is smaller in diameter. The rearward bearing section 125b ends in a conical taper 127. The bearing sections 125a and 125b have substantially the same diameter as those of Bailey, U.S. Pat. No. 5,683,247 but the overall length of the bearing 119 is slightly less than the bearing of either the first embodiment or the Bailey patent.

The bushing 191 is force fit in neck bore 139 to frictionally maintain the bushing, and hence the drive assembly 111, in place in body 103. The bushing 191 includes annular barbs 192 at the front and back thereof. Each barb 192 is about 0.006" thick, and each is set off by annular grooves 193. Each barb is chamfered along its leading edge. Each barb 192 extends about 0.002" to about 0.004" beyond the outer face of the bushing, to prevent removal of the drive assembly from angle body 103 after the bushing 191 is force fitted into the neck bore 139. By way of example, the bushing 191 may have a nominal diameter of 0.227", each annular barb 192 a nominal diameter of 0.231", and the neck bore 139 a nominal diameter of 0.229". This arrangement of barbs and annular grooves has previously been utilized in the commercially available CARE-FREE® prophy angle.

The bushing 191 also incudes a flange 194 at its rearward end. The flange 194 engages rearward end 140 of the neck bore 139 and positions the bushing 191 axially in the neck bore 139. The retainer 131 engages the rear of the bushing and holds the flange 194 in tight engagement with the end 140 of the neck bore 139. It will be seen that the bushing is thus held in place both by the barbs 192 and by the retainer 131. If desired, either the barbs 192 or the retainer 131 may be eliminated.

The drive gear part 117 is thus constrained against axial movement of more than a few thousandths of an inch by the forward end of the bushing 191 and the ball 160.

The bushing 191 also includes a lubricant opening 195 in its side wall, and a double step 196 at the rear of its bore 197. The step 196 reduces the radial clearance with the drive gear shaft to about 0.001" nominal. It also forms a lubricant reservoir at the rear of the bushing 191.

In assembling the drive assembly 111, lubricant is placed in the back of the bushing 191, the drive gear 113 is inserted, and lubricant is then injected through opening 195. The assembly is then press fit into the neck bore 139, and the retainer 131 is forced against the back of the bushing 191.

The ball 160, driven gear 150 and cap 170 are assembled in the same manner as the first embodiment.

The foregoing description is set forth only for illustrative purposes and is not meant to be limiting. Numerous variations within the scope of the appended claims will be apparent to those skilled in the art. For example, the bore in the head of the body may be internally threaded and the cap externally threaded to provide a prophy angle in which the cap can be removed for cleaning and lubricating the driven gear and its chamber. The body may be formed of a suitable plastic which can withstand repeated autoclave cycles, as can the drive gear. The body, and even other parts of the angle, may be formed by casting or molding. Preferably, the cap and the driven gear are formed of materials which can retain the sharpness of the edge of the stem and the critical axial dimension and internal threading of the bur tube. Dental tools other than a prophy cup, such as brushes, could be used; such tools preferably have an elastomeric base part which can form a seal with the stem of the cap. Other seals between the cap and dental tool, such as the seal of FIGS. 1–6 of Richmond, U.S. Pat. No. 3,407,502, may be used, although the preferred seal has been found to provide a particularly long-lasting and positive seal. These examples are merely illustrative.

We claim:

1. A dental prophylaxis angle comprising:
   a one piece body defining a sleeve, a neck, and a head;
   a body bore extending through the neck and the sleeve;
   a head bore in the head, the head bore communicating with the body bore;
   a driven member rotatably mounted in the head bore;
   a drive member rotatably mounted in the sleeve bore, the drive member drivingly engaging the driven member;
   a cap received on the head; and
   a ball in the body, the ball engaging both the drive member and the driven member and limiting axial motion of both the drive member and the driven member.

2. The angle of claim 1 wherein the head bore and the body bore have central axes which intersect, the ball having a center located substantially at the intersection of the axes.

3. The angle of claim 1 wherein the cap is inserted in the head bore, and wherein the driven member is journaled for rotation in the cap.

4. The angle of claim 1 wherein the drive member includes a gear part and a shaft part, and wherein the driven member includes a gear part and a bur tube part.

5. The angle of claim 4 wherein each of the gear parts includes a substantially flat planar surface engaging the ball.

6. The angle of claim 4 wherein the drive member includes a bearing part between the gear part and the shaft part, the bearing part being larger in diameter than gear part.

7. The angle of claim 1 wherein the body, the cap, the drive member, the driven member, and the ball are formed of metal.

8. The angle of claim 1 wherein the body and the cap are made by machining single pieces of metal, and the cap is press fit into the head of the body.

9. The angle of claim 1 wherein the drive member and the driven member are made by machining single pieces of metal.

10. The angle of claim 1 wherein the drive member is directly journaled in the sleeve bore.

11. A dental prophylaxis angle comprising:
    a body defining a sleeve and a head; the sleeve defining a bore which receives a drive member and the head defining a bore which receives a driven member, the head bore and the sleeve bore communicating with each other, the driven member being driven by the drive member; and a cap received in the head bore, the driven member being journaled in the cap, the cap forming the sole rotational bearing for the driven gear, the driven member making substantially point contact with a thrust bearing in the head, rotation of the driven member thereby being substantially unaffected by slight misalignments of the cap with respect to the body.

12. The angle of claim 11 wherein the body defining the sleeve and head is formed in one piece.

13. The angle of claim 11 wherein the thrust bearing is a separate element from the body, inserted in the body.

14. The angle of claim 13 wherein the thrust bearing is a ball.

15. The angle of claim 11 wherein the cap is a metal cap press fit in the head bore.

16. The angle of claim 11 wherein the driven gear comprises an upper bur tube and a lower gear part, the gear part having a larger diameter than the bur tube, an interior of the cap being sized to form a rotational bearing for the lower gear part of the driven gear.

17. The angle of claim 11 further comprising a dental tool operatively connected to the driven member, the dental tool forming a seal with the cap.

18. A dental prophylaxis angle comprising:

a one piece body defining a sleeve, a neck, and a head;

a body bore extending through the neck and the sleeve;

a head bore in the head, the head bore communicating with the body bore;

a driven member rotatably mounted in the head bore;

a drive assembly in the sleeve bore, the drive assembly comprising a drive gear including a gear part at a forward end of the drive assembly, the gear part being operatively connected to the driven member, and a shaft part extending rearwardly from the gear part, the shaft part being sized to be grasped by a collet in a handpiece, and a thrust bearing comprising a sheet-metal retaining ring having a plurality of generally radially extending arms, the arms engaging a wall defining the sleeve bore, the thrust bearing restraining rearward axial movement of the drive assembly.

19. The angle of claim 18 wherein the drive gear is machined from a single piece of metal, the drive gear further comprising a bearing part between the gear part and the shaft part, the bearing part of the drive gear being larger in diameter than the gear part, the bearing part including a relieved central part, the angle further comprising a lubricant contained between the relieved central part and the body bore.

20. The angle of claim 19 wherein the drive gear is directly journaled in the sleeve bore, the bearing part including a rearwardly facing shoulder, and the thrust bearing engaging the rearwardly facing shoulder of the bearing part.

21. The angle of claim 18 wherein the thrust bearing further comprises a washer interposed between the retaining ring and the shoulder on the drive gear.

22. The angle of claim 18 wherein the body bore comprises a forward cylindrical bearing bore, a larger rearward cylindrical skirt bore, and a bearing bore shoulder at a rearward end of the bearing bore, the thrust bearing being mounted against the bearing bore shoulder.

23. The angle of claim 22 wherein the body bore further comprises an intermediate cylindrical bore adjacent the bearing bore shoulder and a tapered bore between the intermediate bore and the skirt bore, the thrust bearing being mounted in the intermediate bore.

24. The angle of claim 22 wherein the drive assembly comprises a bushing, the bearing part of the drive gear being journaled in the bushing, the bushing comprising a flange at a rearward end thereof, the flange abutting the bearing bore shoulder.

25. The angle of claim 18 further including a cap mounted to the head, the driven member being rotatably mounted in the cap, the cap including an opening, the angle also including a dental tool mounted to the driven member, the dental tool having a bottom surface formed of a resilient material, the cap including a knife edge surrounding the opening, the knife edge cutting into the tool bottom surface to create a seal between the tool and the cap.

* * * * *